(12) United States Patent
Halverson et al.

(10) Patent No.: US 8,308,801 B2
(45) Date of Patent: Nov. 13, 2012

(54) SPINAL IMPLANT

(75) Inventors: Peter Halverson, Alpine, UT (US);
Larry L. Howell, Orem, UT (US);
Spencer P. Magleby, Provo, UT (US);
Anton E. Bowden, Lindon, UT (US)

(73) Assignee: Brigham Young University, Provo, UT (US)

( * ) Notice: Subject to any disclaimer, the term of this patent is extended or adjusted under 35 U.S.C. 154(b) by 1221 days.

(21) Appl. No.: 12/029,046

(22) Filed: Feb. 11, 2008

(65) Prior Publication Data

US 2008/0195213 A1 Aug. 14, 2008

Related U.S. Application Data

(60) Provisional application No. 60/901,217, filed on Feb. 12, 2007.

(51) Int. Cl.
*A61F 2/44* (2006.01)
(52) U.S. Cl. .................. 623/17.13; 623/17.15
(58) Field of Classification Search .............. 623/17.15, 623/17.13
See application file for complete search history.

(56) References Cited

U.S. PATENT DOCUMENTS

| | | | |
|---|---|---|---|
| 3,945,053 A | 3/1976 | Hillberry et al. | |
| 5,405,408 A | 4/1995 | Pitkin | |
| 5,415,661 A | 5/1995 | Holmes | |
| 5,733,285 A | 3/1998 | Errico et al. | |
| 5,772,661 A | 6/1998 | Michelson | |
| 5,964,760 A | 10/1999 | Richelsoph | |
| 6,045,552 A | 4/2000 | Zucherman et al. | |
| 6,355,040 B1 | 3/2002 | Richelsoph | |

(Continued)

FOREIGN PATENT DOCUMENTS

DE 10 2006 045 108.2 * 9/2006

(Continued)

OTHER PUBLICATIONS

Jacobsen et al.; "Components for the design of Lamina Emergent Mechanism"; Proceedings of IMECE 2007, 2007 ASME International Mechanical Engineering Congress and Exposition; Nov. 10-16, 2007; Seattle, USA.

(Continued)

*Primary Examiner* — Kevin T Truong
*Assistant Examiner* — David Bates
(74) *Attorney, Agent, or Firm* — Thorpe North & Western LLP

(57) ABSTRACT

Provided is an intervertebral disc prostheses for installation in a spinal column between superior and inferior vertebral bodies. A first intervertebral plate engages one or both of the inferior vertebral endplate and the inferior ring apophysis of the superior vertebral body. A second intervertebral plate engages one or both of the superior vertebral endplate and the superior ring apophysis of the inferior vertebral body. A biaxial rolling-contact core is located between the intervertebral plates. The core includes a convex upper surface and a convex lower surface. The upper surface is curved around a first axis and the lower surface is curved around a second axis that is rotated relative to the first axis. The core is capable of rolling translation relative to the first intervertebral plate along the upper surface and in a first direction, and rolling translation relative to the second intervertebral plate along the lower surface and in a second direction. A flexure constrains the biaxial rolling-contact core to a rolling translation without sliding in at least one of said first direction and said second direction.

23 Claims, 3 Drawing Sheets

U.S. PATENT DOCUMENTS

| | | | |
|---|---|---|---|
| 6,379,354 B1 | 4/2002 | Rogozinski | |
| 6,527,804 B1 | 3/2003 | Gauchet et al. | |
| 6,540,785 B1 | 4/2003 | Gill et al. | |
| 6,572,653 B1 | 6/2003 | Simonson | |
| 6,579,320 B1 | 6/2003 | Gauchet et al. | |
| 6,610,093 B1 | 8/2003 | Pisharodi | |
| 6,645,248 B2 | 11/2003 | Casutt | |
| 6,723,127 B2 | 4/2004 | Ralph et al. | |
| 6,793,678 B2 | 9/2004 | Hawkins | |
| 6,802,867 B2 | 10/2004 | Manasas et al. | |
| 6,811,567 B2 | 11/2004 | Reiley | |
| 6,863,688 B2 | 3/2005 | Ralph et al. | |
| 6,936,071 B1 * | 8/2005 | Marnay et al. | 623/17.15 |
| 6,949,123 B2 | 9/2005 | Reiley | |
| 6,964,666 B2 | 11/2005 | Jackson | |
| 6,966,910 B2 | 11/2005 | Ritland | |
| 6,974,478 B2 | 12/2005 | Reiley et al. | |
| 6,983,924 B2 | 1/2006 | Howell et al. | |
| 6,991,632 B2 | 1/2006 | Ritland | |
| 6,997,955 B2 | 2/2006 | Zubok et al. | |
| 7,029,475 B2 | 4/2006 | Panjabi | |
| 7,074,238 B2 | 7/2006 | Stinson et al. | |
| 7,093,827 B2 | 8/2006 | Culpepper | |
| 7,115,129 B2 | 10/2006 | Heggeness | |
| 7,144,369 B2 | 12/2006 | Bardy | |
| 7,144,396 B2 | 12/2006 | Shluzas | |
| 7,207,992 B2 | 4/2007 | Ritland | |
| 7,229,441 B2 | 6/2007 | Trieu et al. | |
| 7,326,210 B2 | 2/2008 | Jahng et al. | |
| 7,338,398 B2 | 3/2008 | Whiting et al. | |
| 7,361,196 B2 | 4/2008 | Fallin et al. | |
| 7,371,238 B2 | 5/2008 | Soboleski et al. | |
| 7,377,942 B2 | 5/2008 | Berry | |
| 7,445,635 B2 | 11/2008 | Fallin et al. | |
| 7,458,981 B2 | 12/2008 | Fielding et al. | |
| 7,476,238 B2 | 1/2009 | Panjabi | |
| 7,476,251 B2 | 1/2009 | Zucherman et al. | |
| 7,481,830 B2 | 1/2009 | Wall et al. | |
| 7,485,133 B2 | 2/2009 | Cannon et al. | |
| 7,485,134 B2 | 2/2009 | Simonson | |
| 7,485,146 B1 * | 2/2009 | Crook et al. | 623/17.15 |
| 7,491,218 B2 | 2/2009 | Landry et al. | |
| 7,491,238 B2 | 2/2009 | Arnin et al. | |
| 7,491,240 B1 | 2/2009 | Carver et al. | |
| 7,494,507 B2 | 2/2009 | Dixon et al. | |
| 7,537,615 B2 | 5/2009 | Lemair | |
| 7,618,441 B2 | 11/2009 | Groiso | |
| 7,628,814 B2 * | 12/2009 | Studer et al. | 623/17.11 |
| 7,632,292 B2 | 12/2009 | Sengupta et al. | |
| 7,682,375 B2 | 3/2010 | Ritland | |
| 7,785,351 B2 | 8/2010 | Gordon et al. | |
| 7,828,847 B2 * | 11/2010 | Abdou | 623/17.13 |
| 7,892,285 B2 * | 2/2011 | Viker | 623/17.13 |
| 8,025,681 B2 | 9/2011 | Colleran et al. | |
| 2002/0138077 A1 | 9/2002 | Ferree | |
| 2003/0171751 A1 | 9/2003 | Ritland | |
| 2004/0002708 A1 | 1/2004 | Ritland | |
| 2004/0176849 A1 | 9/2004 | Zubok et al. | |
| 2005/0101954 A1 | 5/2005 | Simonson | |
| 2005/0113924 A1 * | 5/2005 | Buttermann | 623/17.13 |
| 2005/0113927 A1 | 5/2005 | Malek | |
| 2005/0125065 A1 | 6/2005 | Zucherman et al. | |
| 2005/0149023 A1 | 7/2005 | Ritland | |
| 2005/0165487 A1 | 7/2005 | Muhanna | |
| 2005/0240270 A1 | 10/2005 | Zubok et al. | |
| 2005/0261772 A1 | 11/2005 | Filippi et al. | |
| 2006/0009768 A1 | 1/2006 | Ritland | |
| 2006/0009850 A1 * | 1/2006 | Frigg et al. | 623/17.13 |
| 2006/0041314 A1 | 2/2006 | Millard | |
| 2006/0052784 A1 | 3/2006 | Dant et al. | |
| 2006/0084987 A1 | 4/2006 | Kim | |
| 2006/0190079 A1 | 8/2006 | Istephanous et al. | |
| 2006/0240533 A1 | 10/2006 | Sengupta et al. | |
| 2006/0271047 A1 | 11/2006 | Jackson | |
| 2006/0271051 A1 | 11/2006 | Berrevoets | |
| 2007/0016193 A1 | 1/2007 | Ritland | |
| 2007/0028714 A1 | 2/2007 | Lusk et al. | |
| 2007/0043365 A1 | 2/2007 | Ritland | |
| 2007/0049936 A1 | 3/2007 | Colleran et al. | |
| 2007/0179618 A1 | 8/2007 | Trieu et al. | |
| 2008/0015588 A1 | 1/2008 | Hawkes | |
| 2008/0077246 A1 * | 3/2008 | Fehling et al. | 623/17.16 |
| 2008/0140075 A1 | 6/2008 | Ensign | |
| 2008/0183209 A1 | 7/2008 | Robinson et al. | |
| 2008/0195208 A1 | 8/2008 | Castellvi | |
| 2009/0005819 A1 | 1/2009 | Ben-Mokhtar et al. | |
| 2009/0048631 A1 | 2/2009 | Bhatnagar et al. | |
| 2009/0228045 A1 | 9/2009 | Hayes et al. | |
| 2009/0259257 A1 | 10/2009 | Prevost | |
| 2009/0270921 A1 | 10/2009 | Krause | |
| 2010/0211106 A1 | 8/2010 | Bowden et al. | |
| 2010/0217324 A1 | 8/2010 | Bowden et al. | |
| 2010/0217326 A1 | 8/2010 | Bowden et al. | |
| 2010/0217334 A1 | 8/2010 | Hawkes | |
| 2010/0222821 A1 | 9/2010 | Bowden et al. | |
| 2010/0222823 A1 | 9/2010 | Bowden et al. | |
| 2010/0241232 A1 | 9/2010 | Halverson et al. | |

FOREIGN PATENT DOCUMENTS

| | | |
|---|---|---|
| KR | 1020050080493 | 8/2005 |
| KR | 1020060113318 | 11/2006 |
| WO | WO 2004/071344 | 8/2004 |
| WO | WO 2005/051243 | 6/2005 |
| WO | WO 2005/107654 | 11/2005 |
| WO | WO 2006127992 | 11/2006 |
| WO | WO 2008/070840 | 6/2008 |
| WO | WO 2008/100891 | 8/2008 |
| WO | WO 2010/096621 | 8/2010 |
| WO | WO 2010/096829 | 8/2010 |
| WO | WO 2010/108010 | 9/2010 |

OTHER PUBLICATIONS

Jacobsen et al.; "Mechanism and Machine Theory"; Mechanism and Machine Theory; 2009; pp. 2098-2109; vol. 44; Elsevier.

Stratton et al.; Force-Displacement Model of the Flexsure™ Spinal Implant; Proceedings of the ASME 2010 International Design Engineering Technical Conferences and Computers and Information in Engineering Conference IDETC/CIE 2010; Aug. 15-18; Montreal, Quebec, Canada.

PCT Application PCT/US2010/025101; filing date Feb. 23, 2010; David Hawkes; ISR mailed Sep. 27, 2010.

PCT Application PCT/US2007/086803; filing date Dec. 7, 2007; Michael D. Ensign; ISR mailed May 19, 2008.

PCT Application PCT/US2008/053661; filing date Feb. 12, 2008; Peter Halverson; ISR mailed Jun. 5, 2008.

PCT Application PCT/US2010/024674; filing date Feb. 19, 2010; Anton E. Bowden; ISR mailed Nov. 19, 2010.

PCT Application PCT/US2010/027826; filing date Mar. 18, 2010; Peter A. Halverson; ISR mailed Jan. 17, 2011.

International Search Report dated Jun. 5, 2008.

Amelie Jeanneau, Just Herder, Thierry Laliberte and Clement Gosselin "A Compliant Rolling Contact Joint and Its Application in a 3-DOF Planar Parallel Mechanism with Kinematic Analysis." Proceedings of DETC'04, ASME 2004 Design Engineering Technical Conferences and Computers and Information in Engineering Conference; Sep. 28-Oct. 2, 2004, Salt Lake City, Utah USA. DETC2004-57264, 2004 by ASME.

Jesse R. Cannon, Craig P. Lusk, Larry L. Howell. "Compliant Rolling-Contact Element Mechanisms." Proceedings of IDETC/CIE 2005, 2005 ASME Design Engineering Technical Conferences & Computers and Information in Engineering Conference, Sep. 24-28, 2005, Long Beach, California, USA. DETC2005-84073.

Peter A. Haverson, Larry L. Howell, Brian D. Jensen, Spencer P. Magleby. "Concepts for Achieving Multi-Stability in Compliant Rolling-Contact Elements." Proceedings of IDETC/CIE 2007, ASME 2007 International Design Engineering Technical Conferences & Computers and information in Engineering Conference, Sep. 24-28, 2007, Las Vegas, USA. DETC2007-34836.

Peter A. Halverson, Larry L. Howell, Spencer P. Magleby. "Tension-based Multi-stable Compliant Rolling-contact Elements." 13th National Conference on Mechanisms and Machines (NaCoMM—2007),IISc, Bangalore, India. Dec. 12-13, 2007.

U.S. Appl. No. 12/709,240, filed Feb. 19, 2010; Anton E. Bowden; office action issued Aug. 29, 2011.
U.S. Appl. No. 12/709,243, filed Feb. 19, 2010; Anton E. Bowden; office action issued Sep. 1, 2011.
U.S. Appl. No. 12/709,248, filed Feb. 19, 2010; Anton E. Bowden; office action issued Sep. 13, 2011.
U.S. Appl. No. 12/709,255, filed Feb. 19, 2010; Anton E. Bowden; office action issued Sep. 15, 2011.
U.S. Appl. No. 12/709,246, filed Feb. 19, 2010; Anton E. Bowden; office action issued Sep. 1, 2011.
U.S. Appl. No. 12/916,110, filed Oct. 29, 2010; Spencer P. Magleby; office action issued Mar. 16, 2012.
U.S. Appl. No. 12/711,131, filed Feb. 23, 2010; David T. Hawkes; office action issued Jun. 4, 2012.
U.S. Appl. No. 12/709,240, filed Feb. 19, 2010; Anton E. Bowden; office action issued Dec. 30, 2011.
U.S. Appl. No. 12/709,240; filed Feb. 19, 2010; Anton E. Bowden; office action dated Jul. 11, 2012.

* cited by examiner

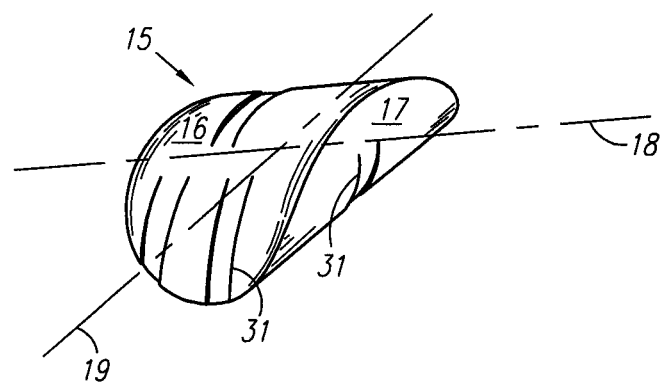
Fig. 7
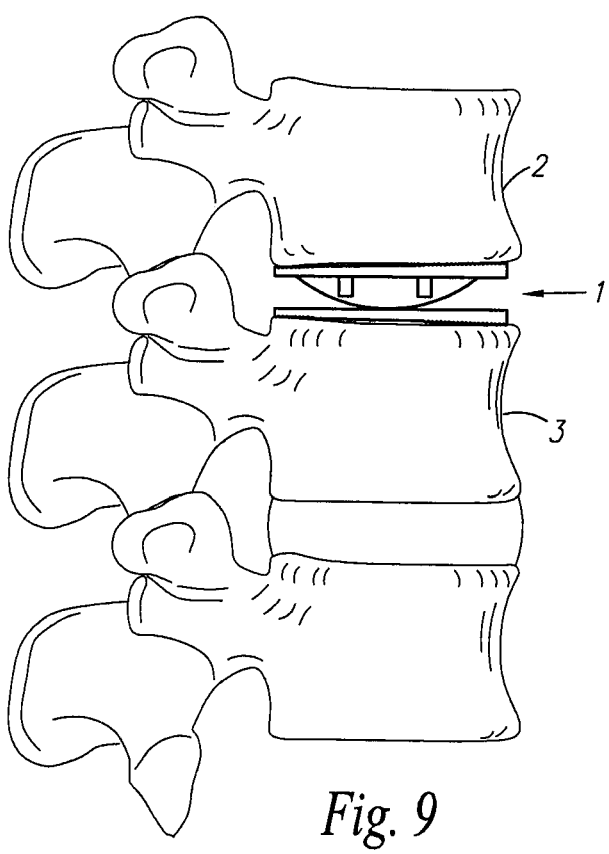
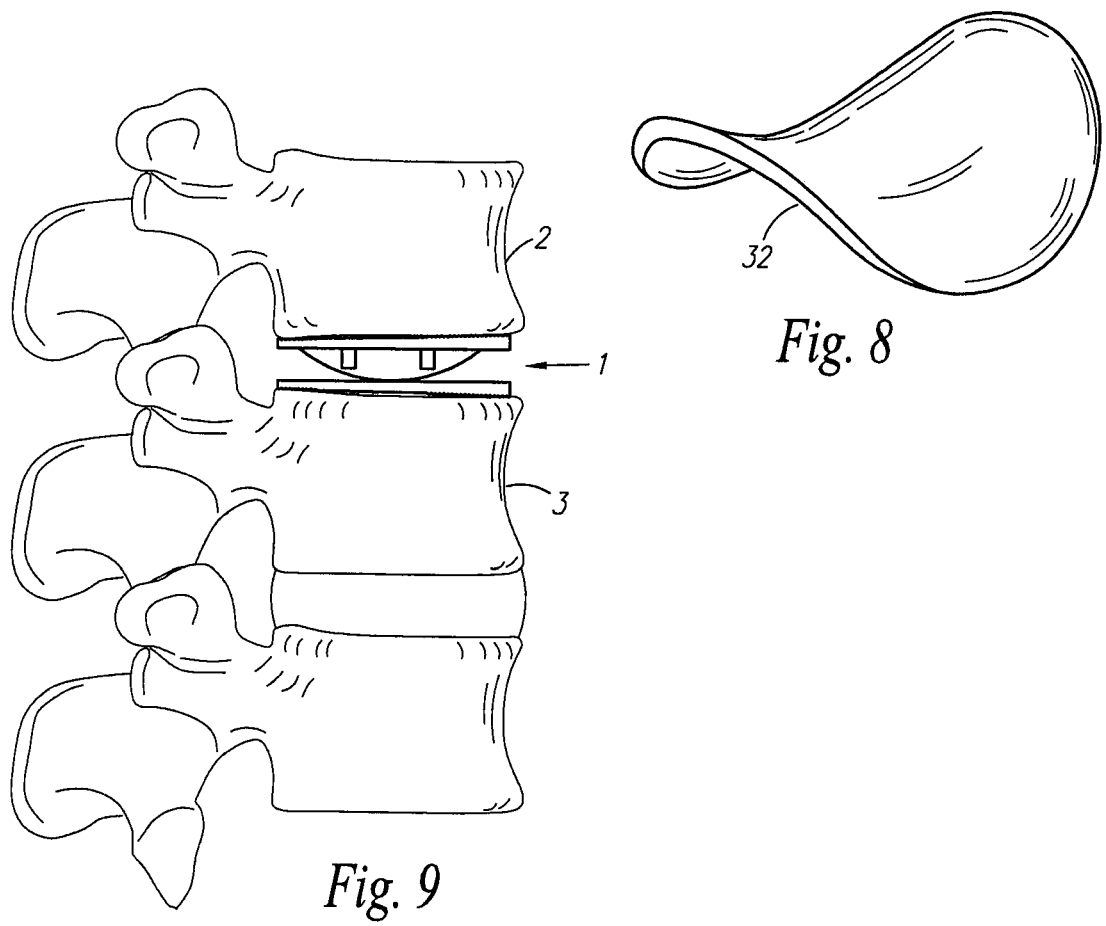
Fig. 8
Fig. 9

SPINAL IMPLANT

CROSS-REFERENCE TO RELATED APPLICATIONS

Benefit of U.S. Provisional Patent Application Ser. No. 60/901,217 filed Feb. 12, 2007, is hereby claimed and the disclosure incorporated herein by reference.

BACKGROUND OF THE INVENTION

1. Field of the Invention

The present invention relates to spinal implants, and, more particularly, to intervertebral disc prostheses.

2. Description of Related Art

The spinal column comprises a series of vertebrae stacked on top of each other. There are typically seven cervical (neck), twelve thoracic (chest), and five lumbar (low back) segments. Each vertebra has a cylindrical shaped vertebral body in the anterior portion of the spine with an arch of bone to the posterior, which covers the neural structures. Each vertebral body includes superior and inferior endplates, which are respectively surrounded by superior and inferior bony rings, called ring apophyses. Between each vertebral body is an intervertebral disc, a cartilaginous cushion to help absorb impact and dampen compressive forces on the spine. To the posterior, the laminar arch covers and protects the neural structures of the spinal cord. At the junction of the arch and anterior vertebral body are articulations to allow movement of the spine.

Various types of problems can affect the structure and function of the spinal column. These can be based on degenerative conditions of the intervertebral disc or the articulating joints, traumatic disruption of the disc, bone or ligaments supporting the spine, tumor or infection. In addition, congenital or acquired deformities can cause abnormal angulation or slippage of the spine. Slippage (spondylolisthesis) anterior of one vertebral body on another can cause compression of the spinal cord or nerves. Patients who suffer from one of more of these conditions often experience extreme and debilitating pain, and can sustain permanent neurological damage if the conditions are not treated appropriately.

One treatment for spinal diseases and injuries is the removal and replacement of the intervertebral disc with a prosthetic device. Some intervertebral prosthetic devices provide a degree of pivotal and rotational movement, while others promote fusion of adjacent vertebrae. Typical non-fusion prosthetic discs, that provide a degree of pivotal and rotational movement, have rigid attachment members for attaching to adjacent vertebrae. The space between the attachment members is usually occupied by a core that generally includes either one or a plurality of elements that move relative to the fixation elements and/or each other. The elements of the core can be formed from polymers, ceramic materials, metals and combinations thereof. The core can also be formed as a single elastomeric element that provides relative motion between the attachment elements due to its material deformation. However, an elastomeric core may not match the kinetics of a natural disc and can eventually exhibit signs of fatigue. Some artificial disc cores have been proposed that include mechanical elements or mechanisms such as dashpots, springs, gears, dovetails, hinges, cams and bar linkages. Such prosthetic discs may require complicated assembly steps to assemble the attachment members and the core, due to the assembly of a large number of parts, and may tend to wear out over time as various mechanical elements fail. Further, conventional prosthetic discs may not replicate the quality or range of natural spinal movement to an acceptable degree. It would be desirable to provide an intervertebral disc prosthesis having a minimum number of separate components, which tends to resist component wear, and which replicates natural spinal movements as closely as possible.

BRIEF SUMMARY OF THE INVENTION

In accordance with one aspect of the present invention, provided is an intervertebral disc prostheses for installation in a spinal column between a superior vertebral body and an inferior vertebral body. A first intervertebral plate engages one or both of the inferior vertebral endplate and the inferior ring apophysis of the superior vertebral body. A second intervertebral plate engages one or both of the superior vertebral endplate and the superior ring apophysis of the inferior vertebral body. A biaxial rolling-contact core is located between the intervertebral plates. The biaxial rolling-contact core includes a convex upper surface and a convex lower surface. The convex upper surface is curved around a first axis and the convex lower surface is curved around a second axis that is rotated relative to the first axis. The biaxial rolling-contact core is capable of rolling translation relative to the first intervertebral plate along the convex upper surface and in a first direction, and rolling translation relative to the second intervertebral plate along the convex lower surface and in a second direction. A first flexure constrains the biaxial rolling-contact core to a rolling translation without sliding in at least one of said first direction and said second direction.

In accordance with another aspect of the present invention, provided is an intervertebral disc prostheses for installation in a spinal column between a superior vertebral body and an inferior vertebral body. A first intervertebral plate engages one or both of the inferior vertebral endplate and the inferior ring apophysis of the superior vertebral body. A second intervertebral plate engages one or both of the superior vertebral endplate and the superior ring apophysis of the inferior vertebral body. A saddle-shaped biaxial rolling-contact core is located between the intervertebral plates. The saddle-shaped biaxial rolling-contact core includes an upper bearing surface and a lower bearing surface. The saddle-shaped biaxial rolling-contact core is capable of rolling translation relative to the first intervertebral plate along the upper bearing surface and in a first direction, and rolling translation relative to the second intervertebral plate along the lower bearing surface and in a second direction. A first flexure constrains the saddle-shaped biaxial rolling-contact core to a rolling translation without sliding in at least one of said first direction and said second direction.

In accordance with another aspect of the present invention, provided is an intervertebral disc prostheses for installation in a spinal column between a superior vertebral body and an inferior vertebral body. A first intervertebral plate engages one or both of the inferior vertebral endplate and the inferior ring apophysis of the superior vertebral body. A second intervertebral plate engages one or both of the superior vertebral endplate and the superior ring apophysis of the inferior vertebral body. A biaxial rolling-contact core is located between and engages the intervertebral plates and includes a convex upper surface and a convex lower surface. The convex upper surface is curved around a first axis and the convex lower surface is curved around a second axis that is perpendicular to and intersects the first axis. The biaxial rolling-contact core is capable of rolling translation relative to the first intervertebral plate along the convex upper surface and in a first direction, and rolling translation relative to the second intervertebral plate along the convex lower surface and in a second direction. A first plurality of flexures is attached to both of the first intervertebral plate and the biaxial rolling-contact core, and partially wrap around the biaxial rolling-contact core. The first plurality of flexures constrain the biaxial rolling-contact core to a rolling translation without sliding in said first direction and exert forces on one or both of the biaxial rolling-contact core and the first intervertebral plate that resist rolling translation of the biaxial rolling-contact core in the first direction. A second plurality of flexures is attached to both of the second intervertebral plate and the biaxial rolling-contact core, and partially wrap around the biaxial rolling-contact core. The second plurality of flexures constrain the biaxial rolling-contact core to a rolling translation without sliding in said second direction and exert forces on one or both of the biaxial rolling-contact core and the second intervertebral plate that resist rolling translation of the biaxial rolling-contact core in the second direction.

BRIEF DESCRIPTION OF THE DRAWINGS

FIG. 7 is a perspective view of a core for the intervertebral disc prosthesis;

FIG. 8 is a perspective of another core for the intervertebral disc prosthesis; and FIG. 9 shows the intervertebral disc prosthesis installed in a spinal column.

DETAILED DESCRIPTION OF THE INVENTION

Figure 1:
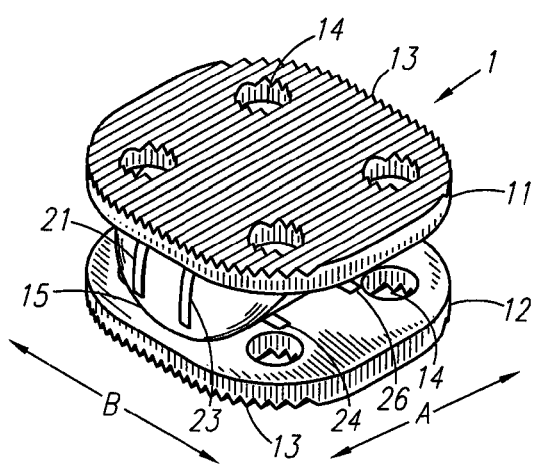
FIG. 1 is a perspective view of an example embodiment of an intervertebral disc prosthesis.

The present invention relates to spinal implants, such as intervertebral disc prostheses. The present invention will now be described with reference to the drawings, wherein like reference numerals are used to refer to like elements throughout. It is to be appreciated that the various drawings are not necessarily drawn to scale from one figure to another nor inside a given figure, and in particular that the size of the components are arbitrarily drawn for facilitating the understanding of the drawings. In the following description, for purposes of explanation, numerous specific details are set forth in order to provide a thorough understanding of the present invention. It may be evident, however, that the present invention can be practiced without these specific details. Additionally, other embodiments of the invention are possible and the invention is capable of being practiced and carried out in ways other than as described. The terminology and phraseology used in describing the invention is employed for the purpose of promoting an understanding of the invention and should not be taken as limiting.

Figure 2:
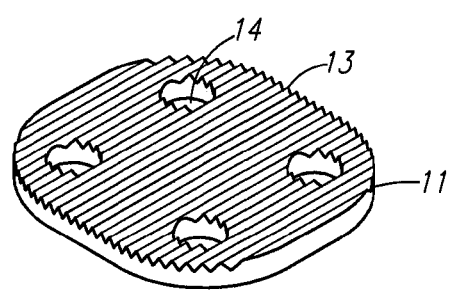
FIG. 2 is an exploded perspective view of the intervertebral disc prosthesis.
Figure 2:
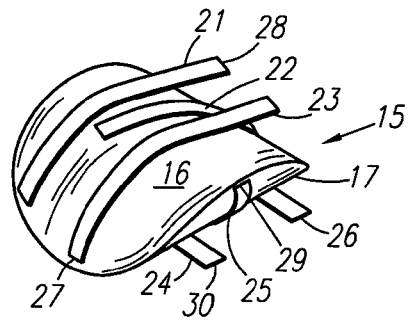
Figure 2:
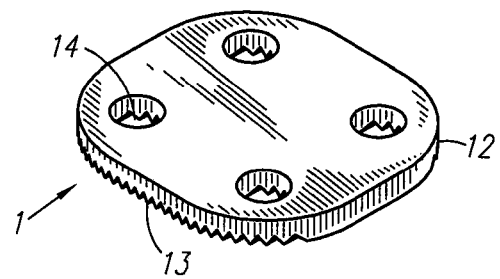
Figure 3:
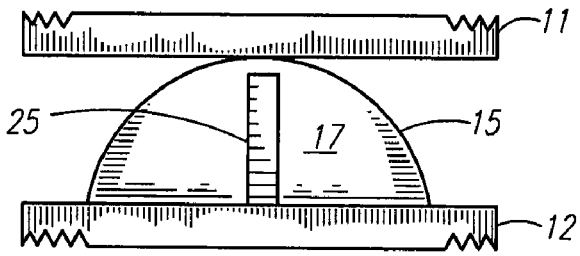
FIG. 3 is a front elevation view of the intervertebral disc prosthesis.
Figure 4:
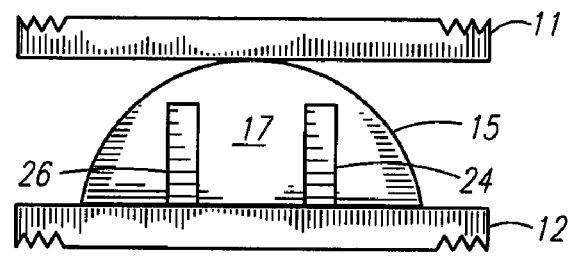
FIG. 4 is a rear elevation view of the intervertebral disc prosthesis.
Figure 5:
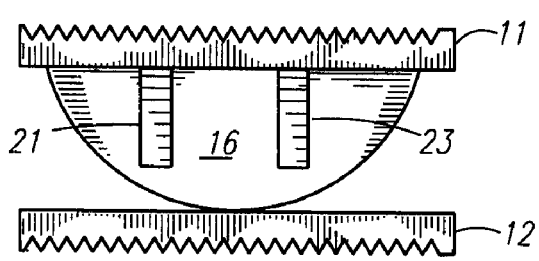
FIG. 5 is a side elevation view of the intervertebral disc prosthesis.
Figure 6A:
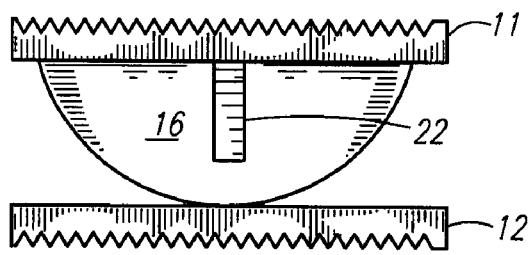
FIG. 6a is a side elevation view of the intervertebral disc prosthesis.
Figure 6B:
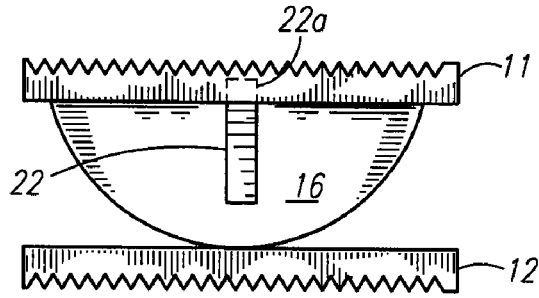
FIG. 6b is a side elevation view of the intervertebral disc prosthesis.

An example embodiment of an intervertebral disc prosthesis 1 for installation in a spinal column is shown in perspective in FIG. 1, in exploded perspective in FIG. 2, in front elevation in FIG. 3, in rear elevation in FIG. 4, in side elevation in FIGS. 5 and 6a, and installed in a spinal column in FIG. 9. As shown in FIG. 9, the intervertebral disc prosthesis 1 is designed to be inserted been adjacent superior (upper) 2 and inferior (lower) 3 vertebral bodies, to replace a removed disc. The intervertebral disc prosthesis 1 could be inserted between adjacent vertebral bodies either anteriorly, posteriorly, or laterally if desired.

The intervertebral disc prosthesis 1 includes a first intervertebral plate 11 and a second intervertebral plate 12. The first intervertebral plate 11 engages the superior vertebral body. More specifically, the first intervertebral plate 11 engages one or both of the inferior vertebral endplate of the vertebral body and the inferior ring apophysis of the vertebral body. The second intervertebral plate 12 engages an adjacent, inferior vertebral body. More specifically, the second intervertebral plate 12 engages one or both of the superior vertebral endplate of the adjacent vertebral body and the superior ring apophysis of the adjacent vertebral body. It is to be appreciated that the first and second intervertebral plates 11, 12 could engage other verbebral portions such as a pedicle or spinous process, for example.

The intervertebral plates 11, 12 can have a generally planar shape. Alternatively, the intervertebral plates 11, 12 can have a curved shape, to better match the contour of the vertebra to which they are attached or accommodate a biaxial rolling-contact core 15 (discussed in detail below). For example, each plate 11, 12 could have one or more convex and/or concave portions. The plates 11, 12 can also have thicker and thinner portions, such as a tapered profile, for example.

The intervertebral plates 11, 12 include a plurality of teeth 13 for anchoring the plates 11, 12 to their respective vertebrae. In an example embodiment, the intervertebral plates 11, 12 have serrations, which provide a saw-toothed side or front profile, and which allow the plates to dig into and thereby anchor to adjacent vertebrae. The plurality of teeth 13 can also be in the form of a plurality of pointed spikes.

In an example embodiment, the intervertebral plates 11, 12 include a plurality of apertures 14 or recessed portions. The apertures 14 or recessed portions permit bone growth from a vertebral surface into the intervertebral plates 11, 12. The intervertebral plates 11, 12 can also be coated with a porous material, to permit bone growth into the porous material from a vertebral surface. For example, the intervertebral plates 11, 12 can include a hydroxyapatite coating.

Example materials of construction for the intervertebral plates 11, 12 include metals such as stainless steel, titanium alloys, for example Ti6Al4V, cobalt alloys/superalloys, or cobalt-chrome-molybdenum alloys, shape memory alloys (SMA), such as nitinol, and bio-inert polymers, for example, carbon reinforced polymers and polyetheretherketones (PEEK), such as the PEEK-OPTIMA® product, which is commercially available from Invibio, Ltd.

The intervertebral disc prosthesis 1 includes a biaxial rolling-contact core 15 located between the intervertebral plates. In an embodiment, the core 15 has a convex upper surface 16 and a convex lower surface 17. The convex upper surface 16 is curved about or around a first axis 18 (see FIG. 7), and the convex lower surface 17 is curved about or around a second axis 19. In an embodiment and as shown in FIG. 7, the axes 18, 19 can intersect, and the intersection can be perpendicular. However, it is to be appreciated that the axes 18, 19 do not have to intersect. For example, the axes can be transverse (i.e., oriented in perpendicular directions) but not intersect, with one axis passing over another. Further, the axes 18, 19 can be relatively oriented at angles other than 90 degrees. The radius of curvature of the convex upper surface 16 and convex lower surface 17 can be equal or unequal, and can be either constant or non-constant. As shown in FIG. 3, the core 15 can have a semicircular profile in an embodiment. Other profiles are possible, such as a semielliptical profile, or a profile with flattened, relatively straight portions, for example. The convex upper surface 16 and convex lower surface 17 can have differently shaped profiles.

The biaxial rolling-contact core 15 is capable of rolling translation in a first direction, which can be a back and forth direction as indicated by arrow A in FIG. 1. The translation in the first direction is relative to the first intervertebral plate 11. In the embodiment of FIG. 1, the translation is lateral and corresponds to lateral or side-to-side spinal bending. However, it is to be appreciated that rolling translation in other directions could be provided, depending on the orientation of the first axis 18. The convex upper surface 16 rolls along the underside of the first intervertebral plate 11, or the first intervertebral plate 11 pivots around the convex upper surface 16. Therefore, little friction is generated as the core 15 moves relative to the first intervertebral plate 11. In an embodiment, the core 15 is capable of rolling translation relative to the first intervertebral plate 11 in only one back and forth direction, for example, back and forth in the direction of arrow A, and the core 15 prohibits rolling translation in other back and forth directions.

The biaxial rolling-contact core 15 is also capable of rolling translation in a second direction, which can be a back and forth direction as indicated by arrow B in FIG. 1. The translation in the second direction is relative to the second intervertebral plate 12. In the embodiment of FIG. 1, the translation is anterior and posterior and corresponds to front-to-back spinal bending. However, it is to be appreciated that rolling translation in other directions could be provided, depending on the orientation of the second axis 19. The convex lower surface 17 rolls along the upper surface of the second intervertebral plate 12, or the second intervertebral plate 12 pivots around the convex lower surface 17. Therefore, little friction is generated as the core 15 moves relative to the second intervertebral plate 12. In an embodiment, the core 15 is capable of rolling translation relative to the second intervertebral plate 12 in only one back and forth direction, for example, back and forth in the direction of arrow B, and the core 15 prohibits rolling translation in other back and forth directions.

Because the biaxial rolling-contact core 15 is capable of rolling translation relative to the first and second intervertebral plates 11, 12, little friction or wearing will be experienced by the core and plates. It is to be appreciated that the biaxial rolling-contact core 15 permits a wide range of relative movement between the first and second intervertebral plates, to permit spinal flexion, extension and lateral bending when the prosthesis 1 is installed.

As stated above, the convex upper surface 16 and convex lower surface 17 can have different shapes. The exact shape of each surface 16, 17 can be specifically designed or engineered to provide a desired range of motion, instantaneous axis of rotation, helical axis of motion, kinematic response, resistance to motion, etc.

The biaxial rolling-contact core 15 can be made of an elastomeric material, so that the core 15 is resilient and provides a degree of shock absorption for compressive forces applied to the intervertebral plates 11, 12. The core 15 can also be made of a more rigid material, such as a hard synthetic polymeric material, for example high density polyethylene (HDPE), cross-linked ultra-high molecular weight polyethylene (UHMWPE), nylon, reinforced polymers, or polyetheretherketones (PEEK), such as the PEEK-OPTIMA® product. The core can also be made of a metallic material, such as stainless steel, titanium alloys or cobalt-chrome-molybdenum alloys.

As best seen in the exploded perspective view of FIG. 2, the prosthesis includes a plurality of flexures 21, 22, 23, 24, 25, 26. Six flexures are shown in FIG. 2, however, it is to be appreciated that the prosthesis 1 can have fewer or more than six flexures. Three of the flexures 21, 22, 23 are associated with the convex upper surface 16 and three of the flexures 24, 25, 26 are associated with the convex lower surface 17. It is to be appreciated that fewer or more than three flexures can be associated with each of the convex upper surface 16 and the convex lower surface 17 and that the convex surfaces 16, 17 can have different numbers of associated flexures.

The flexures 21-26 can be formed as flexible ribbons or bands, which can be elastic or non-elastic. The flexures 21-26 can be resilient and spring-like, tending to resist bending, but returning to their original shape after bending. The flexures 21-26 can be made of a synthetic polymeric material, or a metallic material, or combinations thereof.

The flexures 21, 22, 23 that are associated with the convex upper surface 16 constrain the biaxial rolling-contact core 15 to rolling translation without sliding, and the rolling translation is relative to the first intervertebral plate 11. Similarly, the flexures 24, 25, 26 that are associated with the convex lower surface 17 constrain the biaxial rolling-contact core 15 to rolling translation without sliding, and the rolling translation is relative to the second intervertebral plate 12. Together the flexures 21-26 prevent the core 15 from sliding against the intervertebral plates 11, 12 during flexion, extension and/or lateral bending of the spine.

In an embodiment, the flexures 21, 22, 23 that are associated with the convex upper surface 16 are attached to the biaxial rolling-contact core 15 at one end 27 of the flexure, and are attached to the first intervertebral plate 11 at the other end 28 of the flexure. Similarly, the flexures 24, 25, 26 that are associated with the convex lower surface 17 are attached to the biaxial rolling-contact core 15 at one end 29 of the flexure, and are attached to the second intervertebral plate 12 at the other end 30 of the flexure. It is to be appreciated that the flexures 21-26 can be attached to the core 15 and plates 11, 12 at locations other than their ends and at multiple locations, if desired. The flexures 21-26 can be attached to the core 15 and plates 11, 12 by various known means, including mechanical fasteners and gluing. The core 15 and flexures 21-26 could also be formed as one piece, for example, injection molded as one piece, or the flexures 21-26 can be cut from the core 15 with a portion of each flexure remaining attached to the core 15 as a hinge.

As the biaxial rolling-contact core 15 translates relative to the intervertebral plates 11, 12, by rolling along the plates, the flexures 21-26 partially wind around or unwind from the core 15, which constrains the core 15 to rolling without sliding. The flexures 21-26 can be configured to exert forces on the core 15 and/or intervertebral plates 11, 12 that tend to resist rolling translation of the core 15. For example, one or more of the flexures 21-26 can be placed under tension, or act as a resilient spring that resists bending around the core 15.

As shown in FIG. 6a, a portion 22a of a flexure 21-26 can be located within or project from an intervertebral plate. As shown in FIG. 7, the core 15 can include grooves 31 to accommodate and position the flexures 21-26. By locating a portion of a flexure 21-26 within an intervertebral plate and locating other portions of the flexure in a groove 31 along the core 15, the intervertebral plates 11, 12 can be made to directly contact the core 15, thereby minimizing the exposure of the flexures 21-26 to stress due to compressive forces. The prosthesis 1 will experience a range of compressive forces during spinal flexion, extension and lateral bending, and recessing the flexures 21-26 as described will help to directly transfer compressive forces through the core 15 to the intervertebral plates 11, 12 while minimizing the exposure of the flexures 21-26 to such compressive forces.

The intervertebral plates 11, 12, biaxial rolling-contact core 15 and flexures 21-26 form a so-called complaint mechanism. A compliant mechanism is different from a conventional rigid-body mechanism, which transfers or transforms motion, force, energy, etc. using rigid links and movable joints. A compliant mechanism transfers or transforms motion, force, energy, etc. via the deflection of one or more of its segments. A compliant mechanism does not experience the high internal friction and backlash of a conventional rigid-body mechanism. The disclosed prosthesis 1 includes a type of compliant mechanism that uses flexures that conform to rolling bearing surfaces, for example the convex surfaces 16, 17 of biaxial rolling-contact core 15.

The load-displacement behavior of the compliant mechanism can be made to be nonlinear, to better mimic the behavior of a spinal disc in flexion, extension and lateral bending. It is to be appreciated that the shape of the core 15, the shape of surfaces of the intervertebral plates 11, 12 that bear on the core, and the properties of the flexures 21-26 (due to their shape and materials of construction) can be tailored to replicate or alter: natural spinal movements, the force-deflection curve of the spine, an instantaneous axis of rotation, a helical axis of motion, and shock absorbing/energy dissipating capabilities of a spinal disc. Therefore, the properties of a specific prosthesis 1 can be tailored to an individual patient, and a customized prosthesis prescribed for the patient.

The surfaces of the intervertebral plates 11, 12 that bear on the core are shown in the figures as generally flat. However, these surfaces can have other shapes, such as convex and/or concave portions, for example.

An example saddle-shaped biaxial rolling contact core 32 is shown in FIG. 8. The saddle-shaped core 32 generally conforms to the shape of a hyperbolic paraboloid. The saddle-shaped core 32 is capable of rolling translation relative to the first intervertebral plate 11 along an upper bearing surface, and rolling translation relative to the second intervertebral plate 12 along a lower bearing surface. In an embodiment, the saddle-shaped core 32 is deformable or bendable under compression, and resists axial compression along the spine. The saddle-shaped core 32 can have thicker and thinner portions to allow bending under compression only at desired portions of the core 32.

It should be evident that this disclosure is by way of example and that various changes may be made by adding, modifying or eliminating details without departing from the fair scope of the teaching contained in this disclosure. The invention is therefore not limited to particular details of this disclosure except to the extent that the following claims are necessarily so limited.

What is claimed is:

1. An intervertebral disc prosthesis for installation in a spinal column between a superior vertebral body and an inferior vertebral body, comprising:
    a first intervertebral plate for engaging one or both of the inferior vertebral endplate and the inferior ring apophysis of the superior vertebral body;
    a second intervertebral plate for engaging one or both of the superior vertebral endplate and the superior ring apophysis of the inferior vertebral body;
    a biaxial rolling-contact core located between the intervertebral plates, wherein the biaxial rolling-contact core includes a convex upper surface and a convex lower surface, wherein the convex upper surface is curved around a first axis and the convex lower surface is curved around a second axis that is rotated relative to the first axis, and wherein the biaxial rolling-contact core is capable of rolling translation relative to the first intervertebral plate along the convex upper surface and in a first direction, and rolling translation relative to the second intervertebral plate along the convex lower surface and in a second direction; and
    a first flexure, conformable to one of: i) the convex lower surface; or ii) the convex upper surface, the first flexure constraining the biaxial rolling-contact core to restrained rolling translation in a restrained rolling direction without sliding relative to the first and second intervertebral plates in the restrained rolling direction.

2. The intervertebral disc prosthesis of claim 1, wherein the first axis is transverse to the second axis.

3. The intervertebral disc prosthesis of claim 1, wherein the first axis intersects the second axis, and further wherein the first axis and the second axis are perpendicular.

4. The intervertebral disc prosthesis of claim 1, wherein the biaxial rolling-contact core comprises a resilient material.

5. The intervertebral disc prosthesis of claim 1, wherein the biaxial rolling-contact core includes a groove, and a portion of said first flexure is located within the groove.

6. The intervertebral disc prosthesis of claim 1, wherein a portion of said first flexure is located within one of the first intervertebral plate and the second intervertebral plate.

7. The intervertebral disc prosthesis of claim 1, wherein at least one of the convex upper surface and the convex lower surface has a non-constant radius of curvature.

8. The intervertebral disc prosthesis of claim 1, wherein the first flexure constrains the biaxial rolling-contact core to a rolling translation without sliding in said first direction, the intervertebral disc prosthesis further comprising a second flexure, conformable to one of: i) the convex lower surface or ii) the convex upper surface, the second flexure constraining the biaxial rolling-contact core to a rolling translation without sliding relative to the first and second intervertebral plates in said second direction.

9. The intervertebral disc prosthesis of claim 8, wherein: the first flexure exerts a first force on one or both of the biaxial rolling-contact core and the first intervertebral plate, the first force resisting rolling translation of the biaxial rolling-contact core in said first direction, and the second flexure exerts a second force on one or both of the biaxial rolling-contact core and the second intervertebral plate, the second force resisting rolling translation of the biaxial rolling-contact core in said second direction.

10. The intervertebral disc prosthesis of claim 9, wherein a first end of the first flexure is connected to the first intervertebral plate and a second end of the first flexure is connected to the biaxial rolling-contact core, and wherein a first end of the second flexure is connected to the second intervertebral plate and a second end of the second flexure is connected to the biaxial rolling-contact core.

11. The intervertebral disc prosthesis of claim 1, wherein the biaxial rolling-contact core comprises a monolithic biaxial rolling-contact core.

12. The intervertebral disc prosthesis of claim 1, wherein the first flexure is disposed between at least one of the intervertebral plates and the biaxial rolling-contact core.

13. The intervertebral disc prosthesis of claim 1, wherein the first flexure comprises a ribbon flexure that extends at least partially across one of: i) the convex lower surface; and ii) the convex upper surface.

14. The intervertebral disc prosthesis of claim 13, wherein the first flexure comprises a flexible ribbon.

15. An intervertebral disc prosthesis for installation in a spinal column between a superior vertebral body and an inferior vertebral body, comprising:
   a first intervertebral plate for engaging one or both of the inferior vertebral endplate and the inferior ring apophysis of the superior vertebral body;
   a second intervertebral plate for engaging one or both of the superior vertebral endplate and the superior ring apophysis of the inferior vertebral body;
   a saddle-shaped biaxial rolling-contact core located between the intervertebral plates, wherein the saddle-shaped biaxial rolling-contact core includes an upper bearing surface and a lower bearing surface, wherein the saddle-shaped biaxial rolling-contact core is capable of rolling translation relative to the first intervertebral plate along the upper bearing surface and in a first direction, and rolling translation relative to the second intervertebral plate along the lower bearing surface and in a second direction; and
   a first flexure extending at least partially across one of: i) the upper bearing surface; or ii) the lower bearing surface, the first flexure constraining the saddle-shaped biaxial rolling-contact core to a rolling translation in a restrained rolling direction without sliding relative to the first and second intervertebral plates in the restrained rolling direction.

16. The intervertebral disc prosthesis of claim 15, wherein the saddle-shaped biaxial rolling-contact core comprises a resilient material.

17. The intervertebral disc prosthesis of claim 15, wherein a portion of said first flexure is located within one of the first intervertebral plate and the second intervertebral plate.

18. The intervertebral disc prosthesis of claim 17, wherein a first end of the first flexure is connected to the first intervertebral plate and a second end of the first flexure is connected to the saddle-shaped biaxial rolling-contact core.

19. The intervertebral disc prosthesis of claim 15, wherein the first flexure constrains the saddle-shaped biaxial rolling-contact core to a rolling translation without sliding in said first direction, the intervertebral disc prosthesis further comprising a second flexure extending at least partially across another of: i) the upper bearing surface; or ii) the lower bearing surface, the second flexure constraining the saddle-shaped biaxial rolling-contact core to a rolling translation without sliding relative to the first and second intervertebral plates in said second direction.

20. The intervertebral disc prosthesis of claim 19, wherein: the first flexure exerts a first force on one or both of the saddle-shaped biaxial rolling-contact core and the first intervertebral plate, the first force resisting rolling translation of the saddle-shaped biaxial rolling-contact core in said first direction, and the second flexure exerts a second force on one or both of the saddle-shaped biaxial rolling-contact core and the second intervertebral plate, the second force resisting rolling translation of the saddle-shaped biaxial rolling-contact core in said second direction.

21. The intervertebral disc prosthesis of claim 15, wherein the first flexure comprises a ribbon flexure conformable to one of: i) the convex lower surface; and ii) the convex upper surface.

22. An intervertebral disc prosthesis for installation in a spinal column between a superior vertebral body and an inferior vertebral body, comprising:
   a first intervertebral plate for engaging one or both of the inferior vertebral endplate and the inferior ring apophysis of the superior vertebral body;
   a second intervertebral plate for engaging one or both of the superior vertebral endplate and the superior ring apophysis of the inferior vertebral body;
   a biaxial rolling-contact core located between and engaging the intervertebral plates, wherein the biaxial rolling-contact core includes a convex upper surface and a convex lower surface, wherein the convex upper surface is curved around a first axis and the convex lower surface is curved around a second axis that is perpendicular to and intersects the first axis, and wherein the biaxial rolling-contact core is capable of rolling translation relative to the first intervertebral plate along the convex upper surface and in a first direction, and rolling translation relative to the second intervertebral plate along the convex lower surface and in a second direction;
   a first plurality of ribbon flexures that are attached to both of the first intervertebral plate and the biaxial rolling-contact core, and that partially wrap around the biaxial rolling-contact core, wherein the first plurality of ribbon flexures constrain the biaxial rolling-contact core to a rolling translation without sliding in said first direction and exert forces on one or both of the biaxial rolling-contact core and the first intervertebral plate that resist rolling translation of the biaxial rolling-contact core in the first direction; and
   a second plurality of ribbon flexures that are attached to both of the second intervertebral plate and the biaxial rolling-contact core, and that partially wrap around the biaxial rolling-contact core, wherein the second plurality of ribbon flexures constrain the biaxial rolling-contact core to a rolling translation without sliding in said second direction and exert forces on one or both of the biaxial rolling-contact core and the second intervertebral plate that resist rolling translation of the biaxial rolling-contact core in the second direction.

23. The intervertebral disc prosthesis of claim 22, wherein at least some of the pluralities of ribbon flexures are disposed between at least one of the intervertebral plates and the biaxial rolling-contact core.

* * * * *